United States Patent
Finarov

(10) Patent No.: US 8,552,394 B2
(45) Date of Patent: *Oct. 8, 2013

(54) VACUUM UV BASED OPTICAL MEASURING METHOD AND SYSTEM

(75) Inventor: Moshe Finarov, Rehovot (IL)

(73) Assignee: Nova Measuring Instruments Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/358,548

(22) Filed: Jan. 23, 2009

(65) Prior Publication Data

US 2009/0127476 A1   May 21, 2009

Related U.S. Application Data

(63) Continuation of application No. 10/958,665, filed on Oct. 6, 2004, now Pat. No. 7,482,596.

(30) Foreign Application Priority Data

Oct. 9, 2003  (IL) ......................................... 158344

(51) Int. Cl.
    *G01J 1/04*   (2006.01)

(52) U.S. Cl.
     USPC ....................................................... 250/372

(58) Field of Classification Search
     USPC ....................................................... 250/372
     See application file for complete search history.

(56) References Cited

U.S. PATENT DOCUMENTS

| 4,322,165 | A | 3/1982 | Ellebracht et al. |
| 5,225,681 | A | 7/1993 | Falk et al. |
| 6,222,199 | B1 | 4/2001 | Freeouf |
| 6,399,916 | B1 | 6/2002 | Gortler et al. |
| 6,594,025 | B2 | 7/2003 | Forouhi et al. |
| 6,633,364 | B2 | 10/2003 | Hayashi |
| 6,813,026 | B2 | 11/2004 | McAninch |
| 6,970,228 | B1 | 11/2005 | Aoki et al. |
| 2002/0149774 | A1 | 10/2002 | McAninch |
| 2004/0150820 | A1 | 8/2004 | Nikoonahad et al. |
| 2005/0001172 | A1 | 1/2005 | Harrison |

FOREIGN PATENT DOCUMENTS

DE          4237268          6/1993

OTHER PUBLICATIONS

"Variable Angle Spectroscopic Ellipsometer, Vacuum Ultraviolet to Near Infrared" VUV-VASE, J.A. Woollam Co., Inc., Jan. 1, 2003.

*Primary Examiner* — David Porta
*Assistant Examiner* — Carolyn Igyarto
(74) *Attorney, Agent, or Firm* — Browdy and Neimark, PLLC

(57) ABSTRACT

A method and system are presented for use in optical processing of an article by VUV radiation. The method comprises: localizing incident VUV radiation propagation from an optical head assembly towards a processing site on the article outside the optical head assembly and localizing reflected VUV radiation propagation from said processing site towards the optical head assembly by localizing a medium, non-absorbing with respect to VUV radiation, in within the light propagation path in the vicinity of said site outside the optical head assembly. The level of the medium is controlled by measuring the reflected VUV radiation.

10 Claims, 1 Drawing Sheet

VACUUM UV BASED OPTICAL MEASURING METHOD AND SYSTEM

CROSS-REFERENCED TO RELATED APPLICATIONS

The present application is continuation of co-pending parent application Ser. No. 10/958,665, filed Oct. 6, 2004 and claiming priority from Israel application No. 158344, filed Oct. 9, 2003.

FIELD OF THE INVENTION

This invention is generally in the field of optical measurement/inspection techniques, and relates to a vacuum UV optical system and method particularly useful in integrated metrology.

BACKGROUND OF THE INVENTION

Optical measurements of the thickness of thin films, as well as processing of small pattern features, require an optical system operation with shorter wavelengths. The most traditional technique is limited by DUV (Deep Ultra Violet) spectral range (down to 190 nm, or, due to some sources, to 200 nm). The use of shorter wavelengths enables many metrology advantages for thin film applications, but suffers from strong absorption of light by air (and water).

The above problem can be overcome by operating with such short wavelengths under vacuum conditions (the so-called "Vacuum UV" or "VUV") or in the environment of VUV non-absorbing gas like Nitrogen. For example, the VUV ellipsometer, commercially available from J. A. Woollam Co., Inc., operates in the spectral range down to 150 nm. The configuration of this system requires both an article under measurements and an optical system to be located within a sealed enclosure filled by Nitrogen.

This technique, however, is unsuitable for integrated metrology systems, because of the need for a small system size and high throughput. Indeed, such procedures as loading and unloading of an article (wafer) to and from such a sealed enclosure are time consuming, requiring sealing/unsealing of a processing tool, while maintaining a required gas pressure inside.

SUMMARY OF THE INVENTION

There is a need in the art to facilitate VUV processing of articles by providing a novel optical system and method that eliminates the requirement for a sealed enclosure.

The main idea of the present invention consists of localizing a medium non-absorbing for VUV (e.g. noble gas, such as Nitrogen) along an optical path of light propagation towards and from an illuminated location (point) at the time this location is processed (measured). This enables localizing incident VUV radiation propagating from an optical head assembly towards a processing site on the article outside the optical head assembly and localizing reflected VUV radiation propagation from this site towards the optical head assembly.

The term "VUV radiation" signifies radiation of a wavelength shorter than 190 nm. The term "processing" used herein signifies, measuring (e.g., thickness measurements of at least a top layer of the article), inspection, patterning, data reading/recording, etc. A medium non-absorbing VUV radiation will be termed here for simplicity as "noble gas", but it should be understood that this is a non-limiting example.

Thus, according to one aspect of the present invention, there is provided a method for use in optical processing of an article by vacuum UV (VUV) radiation, the method comprising: localizing incident VUV radiation propagation from an optical head assembly towards a processing site on the article outside the optical head assembly and localizing reflected VUV radiation propagation from said processing site towards the optical head assembly by localizing a medium, non-absorbing with respect to VUV radiation, in within the light propagation path in the vicinity of said site outside the optical head assembly.

The medium localization (noble gas environment, e.g., Nitrogen) within the light propagation path in the vicinity of the processing site is achieved by continuously substituting air environment by said medium environment within a space between the optical head assembly and the processed site. This is implemented by continuously passing the medium (noble gas) through a hollow tip-like housing accommodated between the optical head assembly and the article with a small gap (e.g., of about 0.5 mm) between said hollow housing and the article.

The VUV radiation propagates in the optical head assembly through vacuum or noble gas environment.

The level of the VUV non-absorbing medium in the vicinity of the processing site may be controlled by measuring the intensity of the reflected VUV radiation.

The sequential processing of successive sites of the article is achieved by providing a relative displacement between the article and the hollow housing of the light guiding assembly.

According to another aspect of the present invention there is provided an optical system for use in processing an article, the system comprising:
  an optical head assembly configured for propagating vacuum UV (VUV) radiation from a source of the radiation towards the article and propagating the VUV radiation collected from the article towards a detection unit; and
  a VUV radiation guiding assembly that is configured and operable to receive the VUV radiation from the optical head assembly and guide it towards a processing site on the article, and to receive the VUV radiation reflected from the processing site and guide it into the optical head assembly, said guiding assembly comprising inlet and outlet means for a medium, non-absorbing with respect to VUV radiation, to thereby enable continuous passage of said medium therethrough to substitute air environment by said medium environment along a VUV radiation propagation path in between the optical head assembly and the article.

Preferably, the optical head assembly comprises a sealed enclosure. The latter may be filled or flushed with a VUV non-absorbing gas, or may be evacuated. The filling/flushed gas is the same as the gas in the VUV radiation guiding assembly.

More specifically, the present invention is used for measuring in semiconductor wafers and is therefore described below with reference to this specific application. It should however be understood that the principles of the present invention can be used in various other applications.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
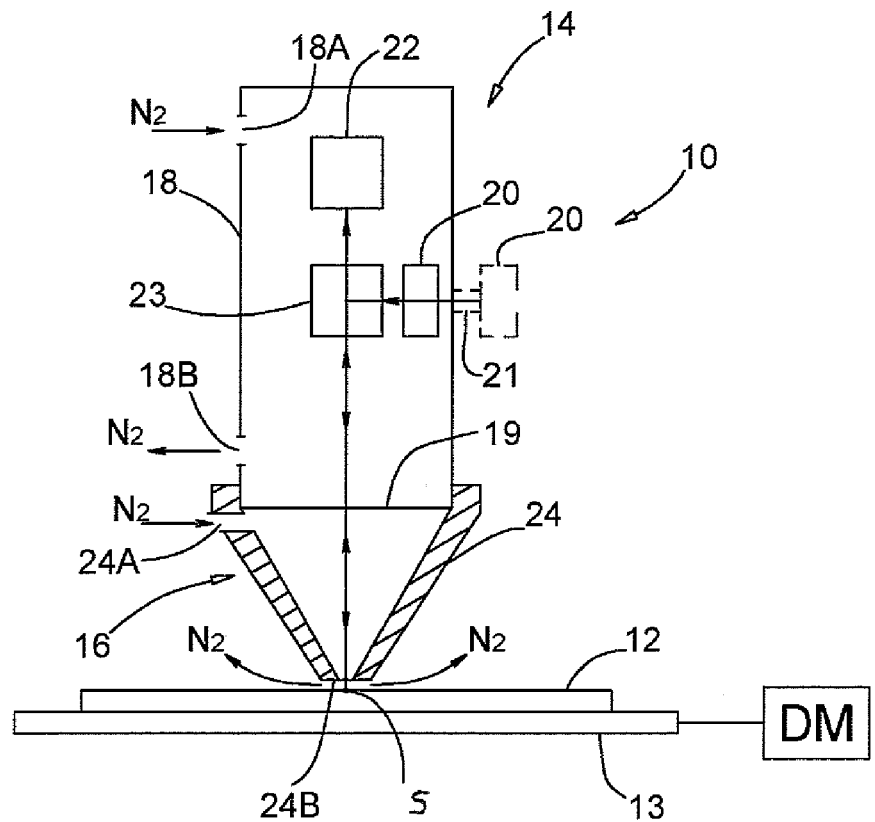
FIG. 1 is a schematic illustration of an optical system according to one embodiment of the invention.

Referring to FIG. 1, there is schematically illustrated an optical system 10 for use in processing (e.g., measuring) an article 12 (e.g., wafer) by VUV radiation (of less than 190 nm wavelength). The article 12 is located on a stage 13 (e.g., X,Y stage or R-Theta stage) and a suitable drive means DM are provided for relative displacement between the article 12 and the system 10. In the present example, the drive means are associated with the stage 13 to move it in a horizontal plane relative to the optical system 10. It should be noted that wafer 12 may be stationary, while the optical system 10 being movable in the horizontal plane.

The system 10 comprises an optical head assembly 14, and a light guiding assembly 16 that is attachable to or integral with the optical head assembly 14. The optical head assembly 14 includes a sealed enclosure 18 which is either filled or flushed with a noble gas (e.g., Nitrogen) via inlet and outlet means 18A and 18B, or evacuated, and includes a light source 20 (e.g., a Deuterium lamp), a light detection unit 22, and a light directing optics (reflective or refractive). The enclosure 18 at its distal end (closer to the article) is formed with an optical window 19 that allows the light propagation towards and from the article 12. The light source may be located inside the sealed enclosure 18, or outside thereof (as shown in the figure in dashed lines) in which case the light is guided from the light source towards the inside of the enclosure via an appropriate waveguide 21. The detection unit 22 comprises one or more photodetectors, for example, a spectrometric detector and an imaging detector, and may also comprise imaging and/or auto-focusing optics. In the present example, the optical head assembly utilizes the normal incidence, i.e., the same optical path for the incident and reflected light propagation. To this end, a beam splitter 23 is used to spatially separate the incident and reflected light beans. It should, however, be noted that the optical head may alternatively utilize the light incidence and detection at a non-zero angle.

The light guiding assembly 16 is associated (attachable or coupled) with the distal end of the sealed enclosure 18, and includes a hollow housing 24 with an noble gas inlet means 24A and an opening 24B at its distal end serving for light propagation and as a gas outlet. The light guiding assembly 16 presents a tip for the local supply and maintenance of noble gas environment along the optical path of light propagation between the optical head assembly 14 and a measurement site S on the article 12. Preferably, the housing 24 has a conical shape (with an open distal end 24B) that fits the geometry of incident and reflected light beams. The housing 24 is preferably made of a material that is non-transparent for UV radiation and does not produce particles that may contaminate the wafer.

The optical system 10 is located relative to the article's plane so as to define a small gap (e.g., of about 0.5 mm) between the housing 24 and the article. To this end, as well as for the light focusing purposes, the stage 13 is also preferably mounted for movement along the Z-axis.

The system 10 operates in the following manner. During the article displacement relative to the optical system, the noble gas environment is maintained in the sealed enclosure 18. The noble gas is continuously flushed into the housing 24 to substitute air and flow through the volume of the housing 24 to be output into the gap through the opening 24B. The noble gas inside the housing 24 thus allows the incident UV light propagation from the optical head to the article and the propagation of the reflected UV radiation to the optical head to be detected. Hence, there is no air above the measurement site S. It should be understood that the dimensions of the housing 24, as well as those of the inlet and outlet openings and gap between the housing and the article, and the operational mode of gas supply, are appropriately selected to desirably replace air environment by noble gas environment within the region between the optical head and the article along the optical path associated with the currently measured site. It should also be noted that the gas environment conditions may be controlled for example by the intensity of detected light signal.

Figure 2:
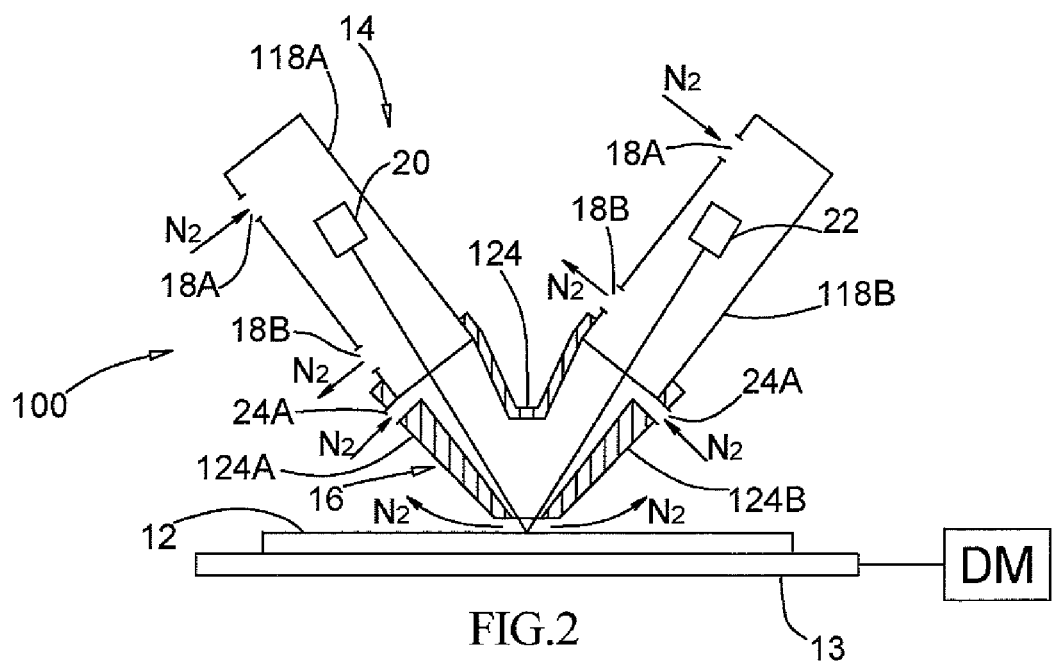
FIG. 2 schematically illustrates an optical system according to another embodiment of the invention.

FIG. 2 exemplifies an optical system 100 according to another embodiment of the invention. The system 100, similarly to system 10, includes an optical head assembly 14 and a light guiding assembly 16, and distinguishes from system 10 in that the optical head assembly is a two part assembly defining separate illuminating and detection channels associated with separate sealed enclosures 118A and 118B, respectively. Each of the sealed enclosures is either evacuated or has noble gas inlet 18A and outlet 18B. One of the sealed enclosures—118A in the present example—serves for the propagation of illuminating radiation and is associated with a light source 20, either internal or external as described above, and the other enclosure 118B contains a detection unit 22 (e.g., spectrometer, ellipsometer, etc.). The light guiding assembly 16 has a hollow housing 124 appropriately configured to define two portions 124A and 124B (separate or integral) that are at one side attachable to or integral with the distal ends of the enclosures 118A and 188B, respectively, and approach the measurement site by the other distal side, where an opening 24B is provided. The housing 124 has one or more gas inlet means 24A.

The system (10 or 100) may also include a gas collection means in the vicinity of the gap between the article and the light guiding assembly. The system of the present invention can be used as a stand alone measurement station and as an integrated measurement machine for processing articles progressing on a production line, e.g., semiconductor wafers, flat panels, etc. The system may utilize the central Nitrogen supply arrangement of a clean room in the semiconductor FAB.

Those skilled in the art will readily appreciate that various modifications and changes can be applied to the embodiments of the invention as hereinbefore described without departing from its scope defined in and by the appended claims.

The invention claimed is:

1. A system for processing a semiconductor wafer of a certain diameter, the system comprising:
   a stage for supporting the wafer being processed;
   an optical system comprising an optical head assembly configured for containing a first medium that is non-absorbing with respect to VUV radiation, the optical head assembly having an optical window for directing VUV radiation from a source of the radiation towards the wafer through said optical window; and
   a light guiding assembly for flowing therethrough a second medium, non-absorbing with respect to VUV radiation, said light guiding assembly being accommodated between said optical head assembly and said stage, and comprising a hollow tip forming an entire outer surface of the light guide assembly that faces the wafer at a processing site, said hollow tip defining at least one optical channel operating to receive the VUV radiation from the optical head assembly and guide the VUV radiation towards the processing site on the wafer supported by the stage, the hollow tip having an end formed with an outlet opening located for discharging said second VUV non-absorbing medium, wherein an outer circumferential dimension of the entire outer surface of the light guide assembly is selected to be smaller than said certain diameter of the wafer being processed.

2. The system of claim 1, wherein a space defined inside said hollow tip is substantially conically shaped.

3. The system of claim 1, wherein said stage is configured as one of the following: x-y stage, z-stage, r-θ stage, or any combination thereof.

4. The system of claim 1, wherein said optical head assembly comprises a sealed enclosure.

5. The system of claim 4, wherein said sealed enclosure is evacuated.

6. The system of claim 4, wherein said medium to be supplied into the optical head assembly comprises a VUV non-absorbing gas.

7. The system of claim 1, wherein said optical system comprises one or more detectors for detecting VUV radiation coming from the wafer.

8. The system of claim 7, wherein said optical system is configured for normal incidence of the VUV radiation onto the wafer.

9. The system of claim 7, wherein said optical system is configured for oblique incidence of the VUV radiation onto the wafer.

10. The system of claim 7, wherein said optical system is configured for spectral measurements.

* * * * *